US011594111B2

(12) United States Patent
Read et al.

(10) Patent No.: US 11,594,111 B2
(45) Date of Patent: Feb. 28, 2023

(54) INTELLIGENT WAKE-UP SYSTEM

(71) Applicant: BOSE CORPORATION, Framingham, MA (US)

(72) Inventors: Jack Read, Bolton, MA (US); Laura Ware, Boston, MA (US); Jonathan Freed, Milton, MA (US); Debra Reich, Arlington, MA (US); Leela Keshavan, Westborough, MA (US); Brian David Mulcahey, Sudbury, MA (US)

(73) Assignee: BOSE CORPORATION, Framingham, MA (US)

( * ) Notice: Subject to any disclaimer, the term of this patent is extended or adjusted under 35 U.S.C. 154(b) by 0 days.

(21) Appl. No.: 15/267,552

(22) Filed: Sep. 16, 2016

(65) Prior Publication Data

US 2018/0082550 A1 Mar. 22, 2018

(51) Int. Cl.
| | |
|---|---|
| *G08B 3/10* | (2006.01) |
| *G04G 21/02* | (2010.01) |
| *G04G 15/00* | (2006.01) |
| *A61B 5/00* | (2006.01) |
| *A61B 5/01* | (2006.01) |
| *A61B 5/0205* | (2006.01) |
| *A61B 5/08* | (2006.01) |

(Continued)

(52) U.S. Cl.
CPC ............... *G08B 3/10* (2013.01); *A61B 5/01* (2013.01); *A61B 5/0205* (2013.01); *A61B 5/08* (2013.01); *A61B 5/4809* (2013.01); *A61B 5/4812* (2013.01); *A61B 5/4815* (2013.01); *G04G 15/003* (2013.01); *G04G 21/025* (2013.01); *A61B 5/0077* (2013.01); *A61B 5/024* (2013.01); *A61B 5/02405* (2013.01); *A61B 5/05* (2013.01); *A61B 5/0816* (2013.01); *A61B 5/11* (2013.01); *A61B 5/6892* (2013.01)

(58) Field of Classification Search
CPC .... G08B 3/10; A61B 5/08; A61B 5/01; A61B 5/6892; A61B 5/11; A61B 5/0205; A61B 5/024
See application file for complete search history.

(56) References Cited

U.S. PATENT DOCUMENTS 4,228,806 A * 10/1980 Lidow ................. A61B 5/0476
368/12
4,377,345 A 3/1983 Yamada et al.
(Continued)

FOREIGN PATENT DOCUMENTS

| CN | 1773563 A | 5/2006 |
|---|---|---|
| CN | 203154531 U | 8/2013 |

(Continued)

OTHER PUBLICATIONS

International Search Report and Written Opinion for application No. PCT/US2017/051513 dated Dec. 13, 2017.
(Continued)

*Primary Examiner* — Ryan W Sherwin
(74) *Attorney, Agent, or Firm* — Lando & Anastasi, LLP

(57) ABSTRACT

A dynamic wake-up alarm is provided-for, including a clock, a contactless biometric sensor, a processor, memory, and a speaker. The processor may be configured to receive a wake-up rule based on at least two wake-up criteria including a time from the clock and data from the biometric sensor, and evaluate whether the criteria are met to activate an alarm.

4 Claims, 6 Drawing Sheets

(51) Int. Cl.
    *A61B 5/024*     (2006.01)
    *A61B 5/05*     (2021.01)
    *A61B 5/11*     (2006.01)

(56) References Cited

U.S. PATENT DOCUMENTS

| | | | |
|---|---|---|---|
| 5,671,733 A | 9/1997 | Raviv et al. | |
| 5,781,640 A | 7/1998 | Nicolino, Jr. | |
| 5,928,133 A * | 7/1999 | Halyak | A61B 5/02 |
| | | | 340/575 |
| 6,236,622 B1 | 5/2001 | Blackman | |
| 6,662,032 B1 | 12/2003 | Gavish et al. | |
| 6,825,769 B2 | 11/2004 | Colmenarez et al. | |
| 6,888,779 B2 | 5/2005 | Mollicone et al. | |
| 7,248,915 B2 | 7/2007 | Ronnholm | |
| 7,637,859 B2 | 12/2009 | Lindback et al. | |
| 7,850,619 B2 | 12/2010 | Gavish et al. | |
| 8,243,937 B2 | 8/2012 | Nicolino, Jr. et al. | |
| 8,280,067 B2 | 10/2012 | Nicolino, Jr. et al. | |
| 8,280,068 B2 | 10/2012 | Nicolino, Jr. et al. | |
| 8,285,344 B2 | 10/2012 | Kahn et al. | |
| 8,379,870 B2 | 2/2013 | Nicolino, Jr. et al. | |
| 8,485,982 B2 | 7/2013 | Gavish et al. | |
| 8,550,978 B2 | 10/2013 | Ullmann | |
| 8,562,526 B2 | 10/2013 | Heneghan et al. | |
| 8,585,607 B2 | 11/2013 | Klap et al. | |
| 8,731,646 B2 | 5/2014 | Halperin et al. | |
| 8,855,334 B1 | 10/2014 | Lavine et al. | |
| 8,870,764 B2 | 10/2014 | Rubin | |
| 8,870,785 B2 | 10/2014 | Muehlsteff et al. | |
| 8,964,997 B2 | 2/2015 | Gauger, Jr. | |
| 8,992,434 B2 | 3/2015 | Halperin et al. | |
| 9,072,437 B2 | 7/2015 | Paalasmaa | |
| 9,192,326 B2 | 11/2015 | Kahn et al. | |
| 9,192,333 B1 | 11/2015 | Hayes et al. | |
| 2002/0080035 A1 | 6/2002 | Youdenko | |
| 2002/0186618 A1 | 12/2002 | Kirkpatrick | |
| 2003/0095476 A1 | 5/2003 | Mollicone et al. | |
| 2003/0142591 A1 | 7/2003 | Baweja et al. | |
| 2005/0152223 A1 | 7/2005 | Kawakami | |
| 2005/0190065 A1 | 9/2005 | Ronnholm | |
| 2006/0017558 A1 | 1/2006 | Albert et al. | |
| 2006/0102171 A1 | 5/2006 | Gavish | |
| 2006/0183980 A1* | 8/2006 | Yang | G16H 20/60 |
| | | | 128/920 |
| 2007/0055115 A1 | 3/2007 | Kwok et al. | |
| 2007/0083079 A1 | 4/2007 | Lee et al. | |
| 2007/0249952 A1 | 10/2007 | Rubin et al. | |
| 2008/0157956 A1 | 7/2008 | Radivojevic et al. | |
| 2009/0231964 A1 | 9/2009 | Kraft et al. | |
| 2009/0287109 A1 | 11/2009 | Ferren et al. | |
| 2009/0292222 A1 | 11/2009 | Ferren et al. | |
| 2010/0039399 A1 | 2/2010 | Kim | |
| 2010/0087701 A1 | 4/2010 | Berka et al. | |
| 2010/0162169 A1 | 6/2010 | Skarp | |
| 2010/0222640 A1 | 9/2010 | Anderson et al. | |
| 2010/0226212 A1 | 9/2010 | Gobindram | |
| 2010/0281982 A1 | 11/2010 | Liao | |
| 2011/0004047 A1 | 1/2011 | Braspenning et al. | |
| 2011/0144455 A1 | 6/2011 | Young et al. | |
| 2011/0224510 A1 | 9/2011 | Oakhill | |
| 2011/0230790 A1 | 9/2011 | Kozlov | |
| 2011/0257772 A1 | 10/2011 | Kerber et al. | |
| 2011/0264164 A1 | 10/2011 | Christopherson et al. | |
| 2012/0092171 A1 | 4/2012 | Hwang et al. | |
| 2012/0327748 A1 | 12/2012 | Lee | |
| 2013/0163394 A1 | 6/2013 | Loree, IV | |
| 2013/0208575 A1* | 8/2013 | Sammut | G04G 13/021 |
| | | | 368/250 |
| 2013/0234823 A1 | 9/2013 | Kahn et al. | |
| 2013/0289419 A1 | 10/2013 | Berezhnyy et al. | |
| 2013/0289431 A1 | 10/2013 | Gavish et al. | |
| 2013/0338446 A1 | 12/2013 | Van Vugt et al. | |
| 2014/0003629 A1* | 1/2014 | Reilly | G06F 3/011 |
| | | | 381/107 |
| 2014/0088373 A1 | 3/2014 | Phillips et al. | |
| 2014/0100904 A1* | 4/2014 | Wolf | G06Q 10/1095 |
| | | | 705/7.19 |
| 2014/0269223 A1* | 9/2014 | Mokhnatkina | G04G 21/025 |
| | | | 368/73 |
| 2014/0275741 A1 | 9/2014 | Vandenbelt et al. | |
| 2014/0334645 A1* | 11/2014 | Yun | G10L 15/08 |
| | | | 381/110 |
| 2014/0371547 A1 | 12/2014 | Gartenberg et al. | |
| 2014/0371635 A1 | 12/2014 | Shinar et al. | |
| 2015/0141852 A1 | 5/2015 | Dusanter et al. | |
| 2015/0164238 A1* | 6/2015 | Benson | G16H 50/30 |
| | | | 340/540 |
| 2015/0173671 A1 | 6/2015 | Paalasmaa et al. | |
| 2015/0230750 A1 | 8/2015 | McDarby et al. | |
| 2015/0258301 A1 | 9/2015 | Trivedi et al. | |
| 2015/0263688 A1 | 9/2015 | Nicolino, Jr. et al. | |
| 2015/0265212 A1* | 9/2015 | Bruekers | A61B 5/6892 |
| | | | 600/301 |
| 2015/0320354 A1 | 11/2015 | Oakhill | |
| 2015/0320588 A1 | 11/2015 | Connor | |
| 2015/0348390 A1 | 12/2015 | Berezhnyy et al. | |
| 2015/0355605 A1 | 12/2015 | Franceschetti et al. | |
| 2015/0367097 A1 | 12/2015 | Gavish | |
| 2015/0382123 A1 | 12/2015 | Jobani | |
| 2016/0005290 A1* | 1/2016 | Takahashi | A61B 5/681 |
| | | | 340/575 |
| 2016/0015315 A1 | 1/2016 | Auphan et al. | |
| 2016/0055842 A1 | 2/2016 | DeFranks et al. | |
| 2016/0058428 A1 | 3/2016 | Shinar et al. | |
| 2016/0151603 A1 | 6/2016 | Shouldice et al. | |
| 2016/0163181 A1 | 6/2016 | Levy et al. | |
| 2016/0165038 A1 | 6/2016 | Lim et al. | |
| 2016/0173943 A1 | 6/2016 | Roberts | |
| 2016/0217672 A1 | 7/2016 | Toon et al. | |
| 2016/0270718 A1 | 9/2016 | Heneghan et al. | |
| 2016/0335886 A1 | 11/2016 | Wei | |
| 2017/0010851 A1* | 1/2017 | Buddhisagar | H04W 68/005 |
| 2017/0039045 A1 | 2/2017 | Abrahami et al. | |
| 2017/0087330 A1 | 3/2017 | Kahn et al. | |
| 2017/0237631 A1* | 8/2017 | Das | H04W 4/06 |
| | | | 370/350 |
| 2018/0078197 A1 | 3/2018 | Ware et al. | |
| 2018/0078198 A1 | 3/2018 | Reich et al. | |
| 2018/0078732 A1 | 3/2018 | Keshavan et al. | |
| 2018/0078733 A1 | 3/2018 | Freed et al. | |
| 2018/0081527 A1 | 3/2018 | Dolecki et al. | |
| 2018/0082550 A1 | 3/2018 | Read et al. | |

FOREIGN PATENT DOCUMENTS

| | | |
|---|---|---|
| CN | 103519784 B | 11/2015 |
| CN | 105142515 A | 12/2015 |
| CN | 105231997 A | 1/2016 |
| CN | 105376408 A | 3/2016 |
| CN | 105592777 A | 5/2016 |
| CN | 105833411 A | 8/2016 |
| EP | 2278507 A2 | 1/2011 |
| EP | 2976993 A2 | 1/2016 |
| FR | 2820230 A1 | 8/2002 |
| JP | 2007244597 A | 9/2007 |
| JP | WO2016121755 A1 | 11/2017 |
| WO | 2005084538 A1 | 9/2005 |
| WO | 2012051630 A2 | 4/2012 |
| WO | 2013093712 A1 | 6/2013 |
| WO | 2013134160 A2 | 9/2013 |
| WO | 2015006364 A2 | 1/2015 |
| WO | 2015008285 A1 | 1/2015 |
| WO | 2015061579 A1 | 4/2015 |
| WO | 2016035073 A1 | 3/2016 |
| WO | 2016122143 A1 | 8/2016 |
| WO | 2016142793 A1 | 9/2016 |

OTHER PUBLICATIONS

International Search Report and Written Opinion for application No. PCT/US2017/051599 dated Jul. 6, 2018.

(56) References Cited

OTHER PUBLICATIONS

Android Headlines: "Samsung Galaxy S5—How to Set an Alarm", YouTube, Apr. 28, 2014, pp. 1-3, XP054978390, Retrieved from the Internet: URL:https://www.youtube.com/watch?v=d8MT5Y5US18.
First Office Action of the State Intellectual Property Office of the People's Republic of China from Chinese Application No. 201780070147.X dated Apr. 13, 2021.
Office Action from Chinese Application No. 201780070140.8 dated Jun. 12, 2020.
Second Office Action and Search Report from Chinese Application No. 201780070140.8 dated Jan. 25, 2021.
"Rise & Shine: Natural Alarm Clock & Sleep System," Serenity Series, 2012, 16 pages, Verilux, China.

* cited by examiner

INTELLIGENT WAKE-UP SYSTEM

CROSS-REFERENCE TO RELATED APPLICATIONS

This application relates to U.S. patent application Ser. No. 15/267,464 entitled Sleep Quality Scoring and Improvement; U.S. patent application Ser. No. 15/267,567 entitled Sleep Assistance Device; U.S. patent application Ser. No. 15/267,848 entitled Sleep System; U.S. patent application Ser. No. 15/267,858 entitled User Interface for a Sleep System; and to U.S. patent application Ser. No. 15/267,886 entitled Sleep Assessment Using a Home Sleep System; all of which are filed on even date herewith and are incorporated herein by reference.

FIELD

This disclosure relates to systems, methods, and apparatuses for helping users wake-up from sleep in a manner that allows users to set dynamic wake-up criteria and thereby maximize sleep.

BACKGROUND

Wake-up alarms use a variety of techniques to help a user wake-up on time. However, wake-up alarms typically only allow users to set times at which they wish to wake-up and do not allow users to set wake-up criteria that will allow the wake-up time to change dynamically under changing conditions. Thus, there exists a need for a wake-up alarm that can wake a user based on the fulfillment of conditions pre-set by a user instead of just time.

SUMMARY

This disclosure relates to systems, methods, and apparatuses for dynamic wake-up alarms.

All examples and features mentioned below can be combined in any technically possible way.

In one example, a dynamic wake-up alarm is provided-for, including a clock, a contactless biometric sensor for determining at least one of a heart rate, a respiratory rate, a presence of a user, or movement of a user, a processor, memory, and a speaker. The processor may be configured to receive a wake-up rule based on at least two wake-up criteria including a time from the clock and data from the biometric sensor, and evaluate whether the criteria are met and activate an alarm based on the evaluation determining that the criteria are met. The wake-up rule may allow the alarm to be activated based on the biometric sensor data only after a time specified by the time criteria is passed. Some examples may include network communications hardware for retrieving information regarding wake-up criteria via a network. In other examples, the processor is further configured to determine from the contactless biometric sensor a state of the user's sleep, and the wake-up criteria include that the user is in a state of light sleep. The processor may also be configured to evaluate a wake-up rule and preclude activation of the alarm based on a determination that the criteria of the wake-up rule are met. In some implementations, the processor is configured to receive information regarding a default timeframe for waking. Wake-up rules may also include at least one additional wake-up criteria for evaluation and an alarm type.

In some examples of the dynamic wake-up alarm, additional wake up criteria may include a traffic condition, a weather condition, a home automation condition, a calendar entry, a biometric indicator of a second user, or a sleep score. An alarm type may also specify that the alarm may be shut off by at least one of a mechanical switch, vacating a sleep space, or waking up.

In some implementations of the dynamic wake-up alarm, the processor may be configured to receive at least one home automation rule based on at least one wake-up criteria, wherein the processor is configured to evaluate the at least one home automation rule and transmit a signal for activating at least one home appliance based on a determination that the wake-up criteria associated with the home automation rule are met.

A method for providing a wake-up alarm may also be provided-for, including receiving a wake-up rule based on at least two wake-up criteria including time and data from a biometric sensor, storing the wake-up rule in an alarm profile, receiving information regarding the current time, retrieving information regarding the wake-up criteria from the biometric sensor, determining whether said wake-up criteria are met, and if the criteria are met, activating an alarm. In some examples, the step of retrieving information regarding wake-up criteria from the biometric sensor comprises reading said contactless biometric sensor and determining at least one of a heart rate, a respiratory rate, a presence of a user, or movement of a user. In some examples, the data from a biometric sensor comprises a sleep score.

In some examples of the method, the wake up rule is based on at least a third wake-up criteria, including a traffic condition, a weather condition, a home automation condition, a calendar entry, or a biometric indicator of a second user. The method may also include retrieving information regarding the at least a third wake-up criteria from a remote database via a network. Other examples include receiving at least one alarm type associated with at least one rule.

Some implementations of the method may also include receiving at least one home automation rule based on at least one wake-up criteria, evaluating whether the wake-up criteria associated with the at least one home automation rule have been met, and transmitting a signal for controlling at least one home appliance based on a determination that the wake-up criteria associated with the at least one home automation rule have been met.

A wake-up alarm system is also provided-for, including a clock, a processor, memory, and a speaker. The processor may be configured to receive at least one wake-up rule based on at least two wake-up criteria including time and data from a biometric sensor. The processor may be further configured to determine whether the wake-up criteria are met and activate an alarm if the criteria are met. In some examples, the data from a biometric sensor may include a sleep score. In other examples, the wake-up alarm system may further include a contactless biometric sensor for determining at least one of a heart rate, a respiratory rate, a presence of a user, or movement of a user. The at least one wake up rule may also be based on at least a third wake-up criteria, including a traffic condition, a weather condition, a home automation condition, a calendar entry, or a biometric indicator of a second user. Some exemplary systems also include network communications hardware for retrieving information regarding wake-up criteria via a network.

In some implementations of the wake-up alarm system, the processor is further configured to receive an alarm type associated with the at least one wake-up rule. Some alarm types may specify that a snooze feature is disabled or a snooze feature is enabled, in some examples. An alarm type may also specify that the alarm may be shut off by at least one of a mechanical switch, vacating a sleep space, or waking up.

In other implementations of the wake-up alarm system, the processor may be configured to receive at least one home automation rule based on at least one wake-up criteria. In such implementations, the processor may be configured to evaluate whether the wake-up criteria associated with said at least one home automation rule has been met and to transmit a signal for controlling at least one home appliance based on a determination that the wake-up criteria associated with the at least one home automation rule has been met.

BRIEF DESCRIPTION OF THE DRAWINGS

Various aspects of at least one implementation of a dynamic wake-up alarm are discussed below with reference to the accompanying figures. The figures are provided for the purposes of illustration and explanation and are not intended as a definition of the limits of the disclosure.

DETAILED DESCRIPTION

It should be understood that the following descriptions are not intended to limit the disclosure to an exemplary implementation. To the contrary, it is intended to cover alternatives, modifications, and equivalents as may be included within the spirit and scope of the described subject matter.

Figure 1A:
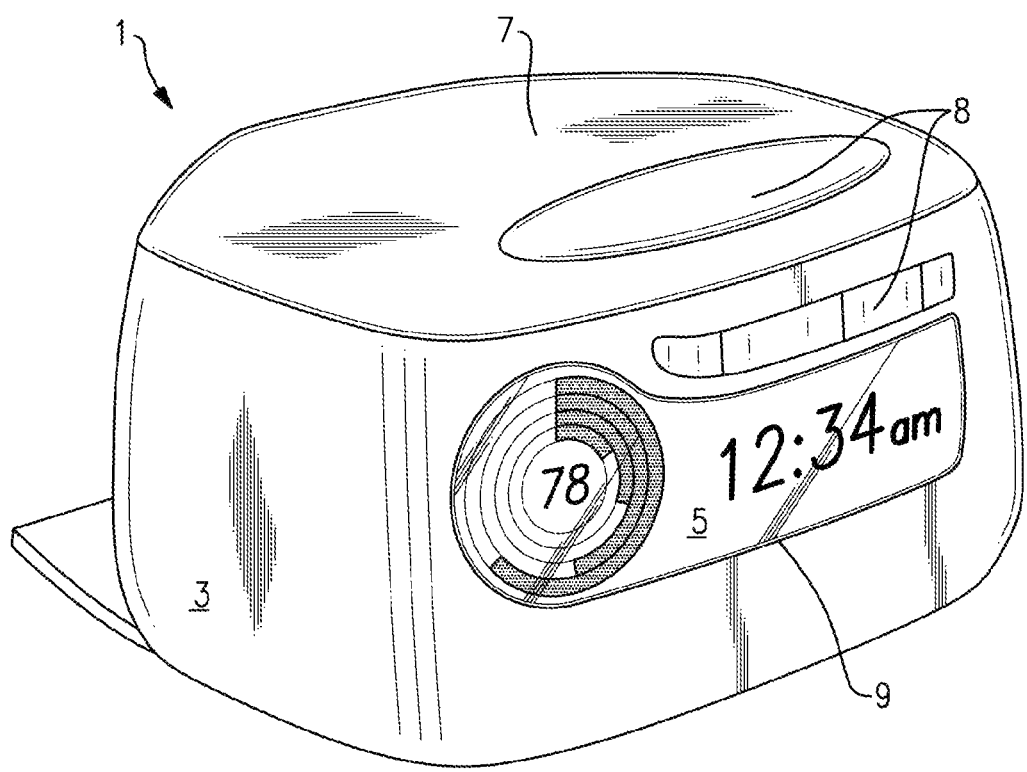
FIG. 1A is a front perspective view of a dynamic wake-up alarm with a rectangular housing in one example of the present disclosure.
Figure 1B:
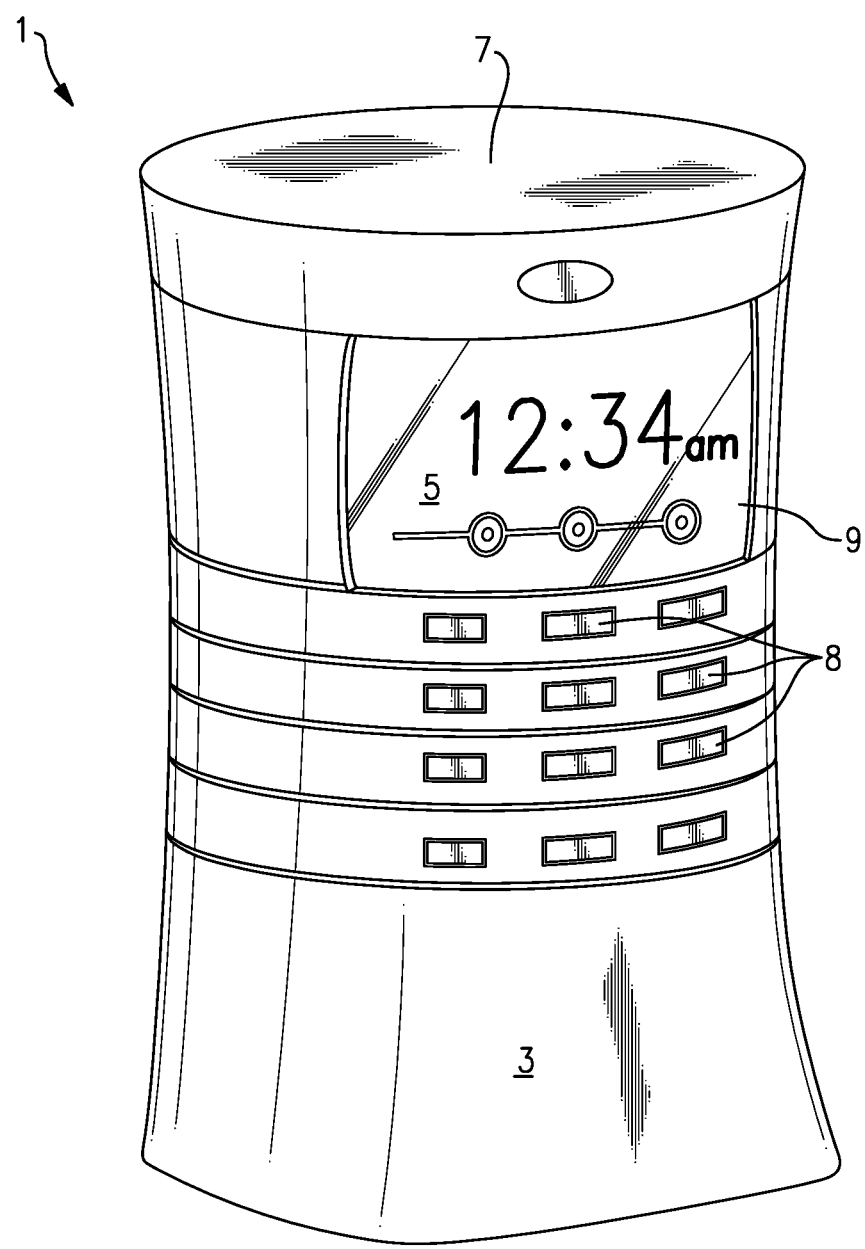
FIG. 1B is a front perspective view of a dynamic wake-up alarm with a cylindrical housing in one example of the present disclosure.
Figure 1C:
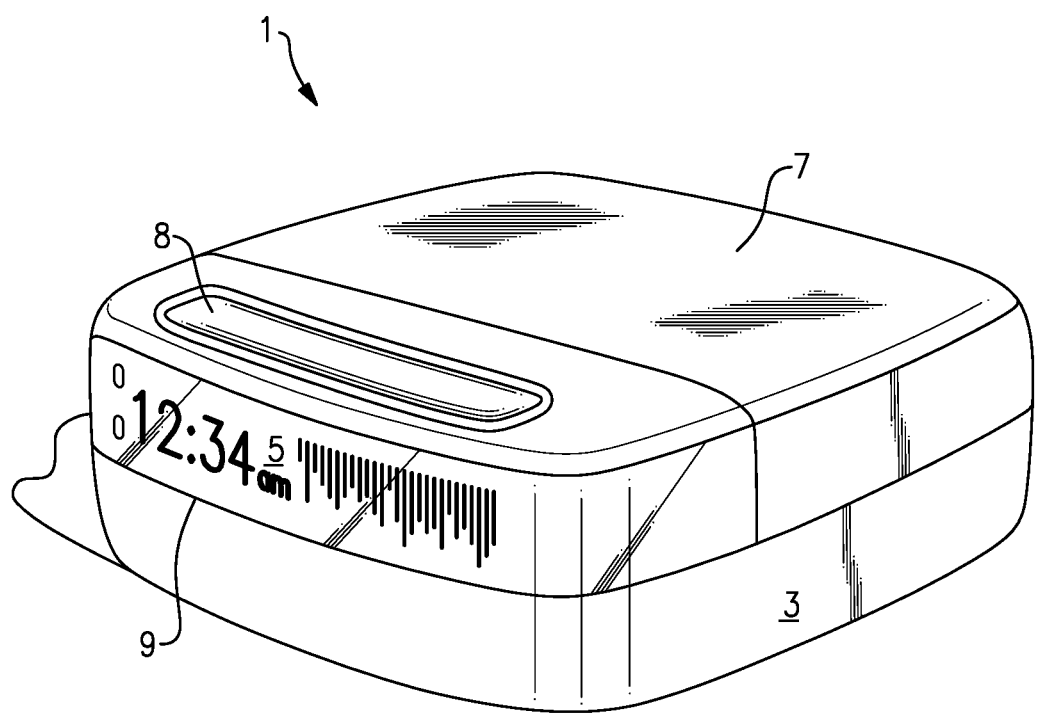
FIG. 1C is a front perspective view of a dynamic wake-up alarm with a square housing in one example of the present disclosure.

FIGS. 1A-1C are front perspective views of a dynamic wake-up alarm 1 in three examples of the present disclosure. As shown, a dynamic wake-up alarm 1 may include a housing 3, a display screen 5, speakers 7, and buttons 8 or a touchscreen 9 for inputting information into the dynamic wake-up alarm. A wide variety of forms may be utilized for a dynamic wake-up alarm, including a rectangular shape (e.g. FIG. 1A), an elongate cylindrical tower (e.g. FIG. 1B), or a flat square shape (e.g. FIG. 1C). However, as one of ordinary skill in the art will appreciate, any suitable form factor may be utilized that may be suitable for being placed nearby a user while sleeping, such as on a night stand, for example. In such examples, housing 3 may be formed into a suitable shape from any rigid materials, including plastics, metals, wood, or composites.

In some examples, display screen 5 may provide biometric or sleep information gathered by dynamic wake-up alarm 1 that may be of interest to a user. Such information may include information regarding the user's biometrics observed during sleep periods, such as information regarding the user's presence, heart rate, heart rate variability, respiratory rate, ambient temperature, movement, snoring, or sleep state over time. This may be direct information or derived information. In some examples, display screen 5 may also include a clock as shown in FIGS. 1A-1C.

Speakers 7 may comprise any suitable speaker system for generating sounds, as may be familiar to one of ordinary skill in the art. In some examples, speakers 7 may comprise an upwards firing driver along with an acoustic deflector, to provide an omni-directional acoustical experience. Such configurations may be helpful for providing non-directional, room-filling sounds for a soundscape or a white noise while a user is sleeping. Omni-directional sounds systems may be particularly helpful to achieve soothing sounds, a natural wake-up experience, and a consistent listening experience throughout the room. As one of ordinary skill in the art will appreciate, any acceptable sound system for speakers 7 may be employed for producing room-filling sounds, however.

Touchscreen 9 or buttons 8 may comprise any suitable means for delivering inputs to dynamic wake-up alarm 1, including a tactile sensor coupled to a surface of housing 3 for detecting the presence of a user's fingers and for detecting pressure, such as when a virtual button on touchscreen 9 is being pressed by a user. Virtual buttons may be displayed on touchpad 9 in a manner familiar to one of ordinary skill in the art in order to allow an operating system to accept input commands from a user. In this manner, dynamic wake-up alarm 1 may be configured to accept input commands in a variety of ways and in a variety of contexts, by providing a programmable user interface that may present options and choices to a user via touchpad 9. In other examples, touchscreen 9 may present a permanent display of fixed virtual buttons or include fixed physical buttons 8 for receiving inputs from a user.

In some examples, display screen 5 and a touchscreen 9 may not be necessary or may be reduced in function because a user's smartphone or other external computing device may be used for linking with dynamic wake-up alarm 1, displaying information from dynamic wake-up alarm 1, accepting inputs, and delivering them to dynamic wake-up alarm 1 in order to control its functions. In such a configuration, the display screen 5 and touchscreen 9, if any, may display and control only typical bedside clock-related functions, such as time, alarm, and music selection, or a simplified component of the sleep score, such as just a total score value, may be displayed.

Figure 2:
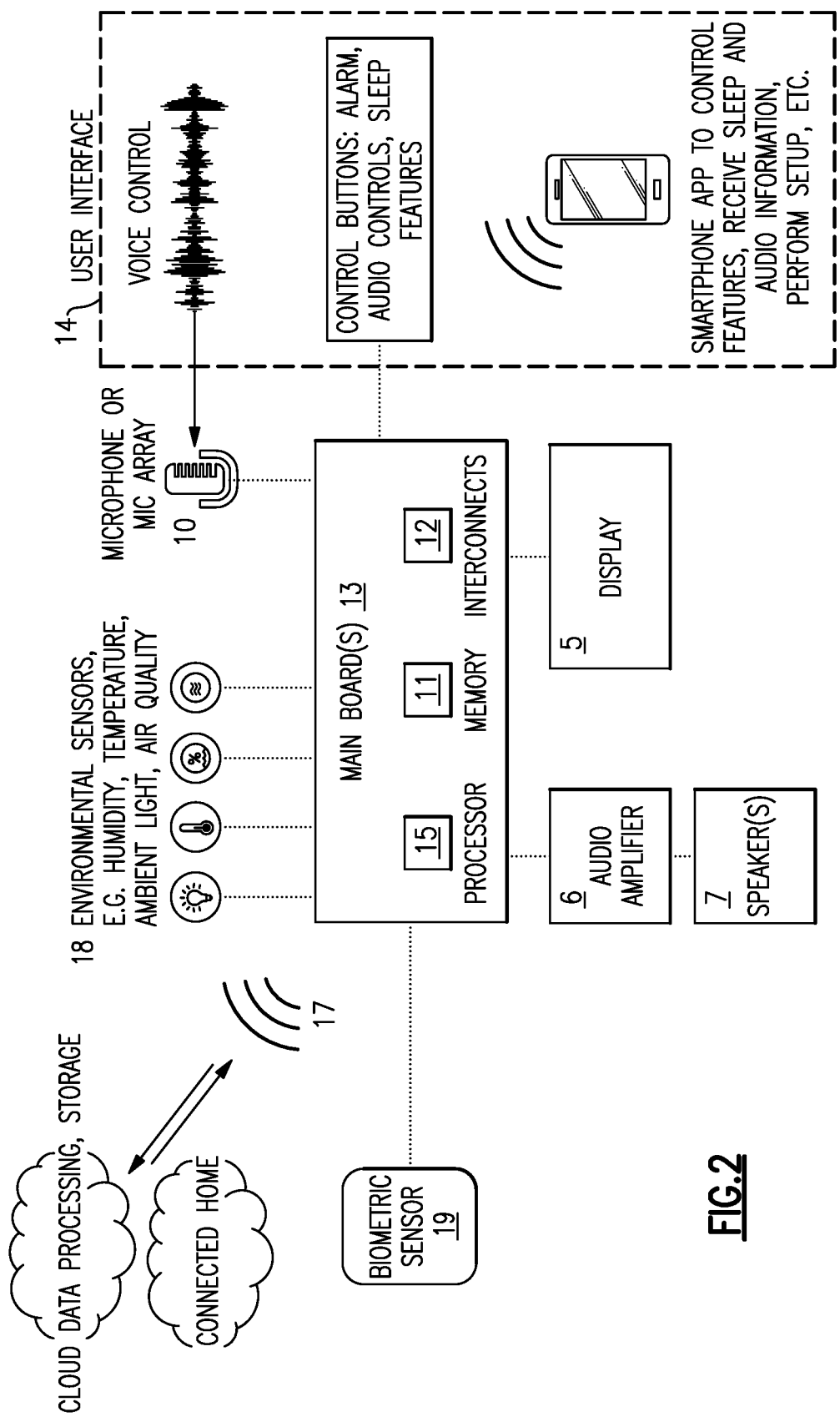
FIG. 2 is a schematic of the components of a dynamic wake-up alarm in one example of the present disclosure.

FIG. 2 provides an exemplary schematic of a dynamic wake-up alarm, showing its components. As shown, dynamic wake-up alarm 1 may include one or more main board(s) 13, including a processor 15, memory 11, and interconnects 12. Main board 13 controls the operation of several other connected components, such as a microphone 10, display screen 5, audio amplifier 6, speakers 7, and buttons 8 or a touchscreen 9 for inputting information into the dynamic wake-up alarm. Communications hardware 17 may include any wired or wireless communication means suitable for use with a dynamic wake-up alarm, such as WiFi, Bluetooth, USB, micro USB, or any suitable wired or wireless communications technologies known to one of ordinary skill in the art. Main board 13 also receives information from biometric sensor 19 as well as any number of environmental sensors 18, for detecting environmental conditions, such as temperature, humidity, ambient light, and air quality. Main board 13 also receives inputs based on a user's interactions with a user interface 14, which may include voice-activated commands detected by microphone 10; various audio, alarm, and sleep control inputs received from buttons 8 or touchscreen 9; or inputs received from a companion application running on a user's smart phone or other external computing device. The communications hardware 17 may also provide communications with external data sources, such as weather reports, and connected home services providing access to such things as lights, thermostat, locks, and any of the sensors 18.

Microphone 10 may be any suitable microphone for detecting and sampling sounds within a user's bedroom or sleep space, as is known to one of ordinary skill in the art. In some examples, microphone 10 may be an arrayed microphone that is suitable for distinguishing between sounds produced by dynamic wake-up alarm 1 and sounds produced externally within the user's bedroom or sleep space. In examples where microphone 10 comprises an arrayed microphone, it may comprise a plurality of omni-directional microphones, directional microphones, or any mixture thereof, distributed about dynamic wake-up alarm 1. Microphone 10 may be coupled to processor 15 for simultaneous processing of the signals from each individual microphone in a manner familiar to one of ordinary skill in the art in order to distinguish between sounds produced by dynamic wake-up alarm 1 and other sounds within the room and to analyze any external noises for use with sound-masking subroutine 27, as discussed below. Microphone 10 may employ beamforming or other techniques to achieve directionality in a particular direction, for example, towards a sound to be analyzed. Microphone 10 may be employed both for monitoring the user's sleep and for receiving spoken user interface commands.

Biometric sensor 19 remotely detects information about a nearby user, including bed presence, respiration rate, heart rate, heart rate variability, or a sleep state among other biometric indicators. In some examples, biometric sensor 19 may be a contactless biometric sensor which may use an RF sensor for directing RF signals towards a user, measuring the strength of the backscattered signal, and analyzing the backscattered signal to determine the state of various vital signs of a user over time. Other contactless biometric techniques may include lasers for measuring minor skin deflections caused by a user's heart rate and blood pressure; or image-based monitoring systems, whereby skin deflections caused by heartbeats and blood pressure may be observed and analyzed over time through a camera. Biometric sensor 19 may be configured to report detected biometric information to processor 15 for storage in memory 11 and to be analyzed for use in the various subroutines described herein.

In other examples, dynamic wake-up alarm 1 may also employ a direct biometric sensor as is known to one of ordinary skill in the art. A direct biometric sensor may include probes or contact pads, that may be disposed on or under the user's body or within their mattress or sheets in order to mechanically detect biometric information, such as movement, respiration, heart rate, blood pressure, and temperature, among others. Such sensors may include accelerometers, other motion sensors, or mechanical sensors such as piezoelectric sensors or other vibration sensors. The biometric information detected by the probes may then be communicated to dynamic wake-up alarm 1 using a wired or wireless connection in a manner known to one of ordinary skill in the art. In some examples, a biometric sensor may be placed within earbuds worn by a user. Other implementations may combine both contactless and direct biometric sensors. Mechanical sensors that measure the body through an intervening medium, such as bedding, are included in the category of "contactless" biometric sensors.

Figure 3:
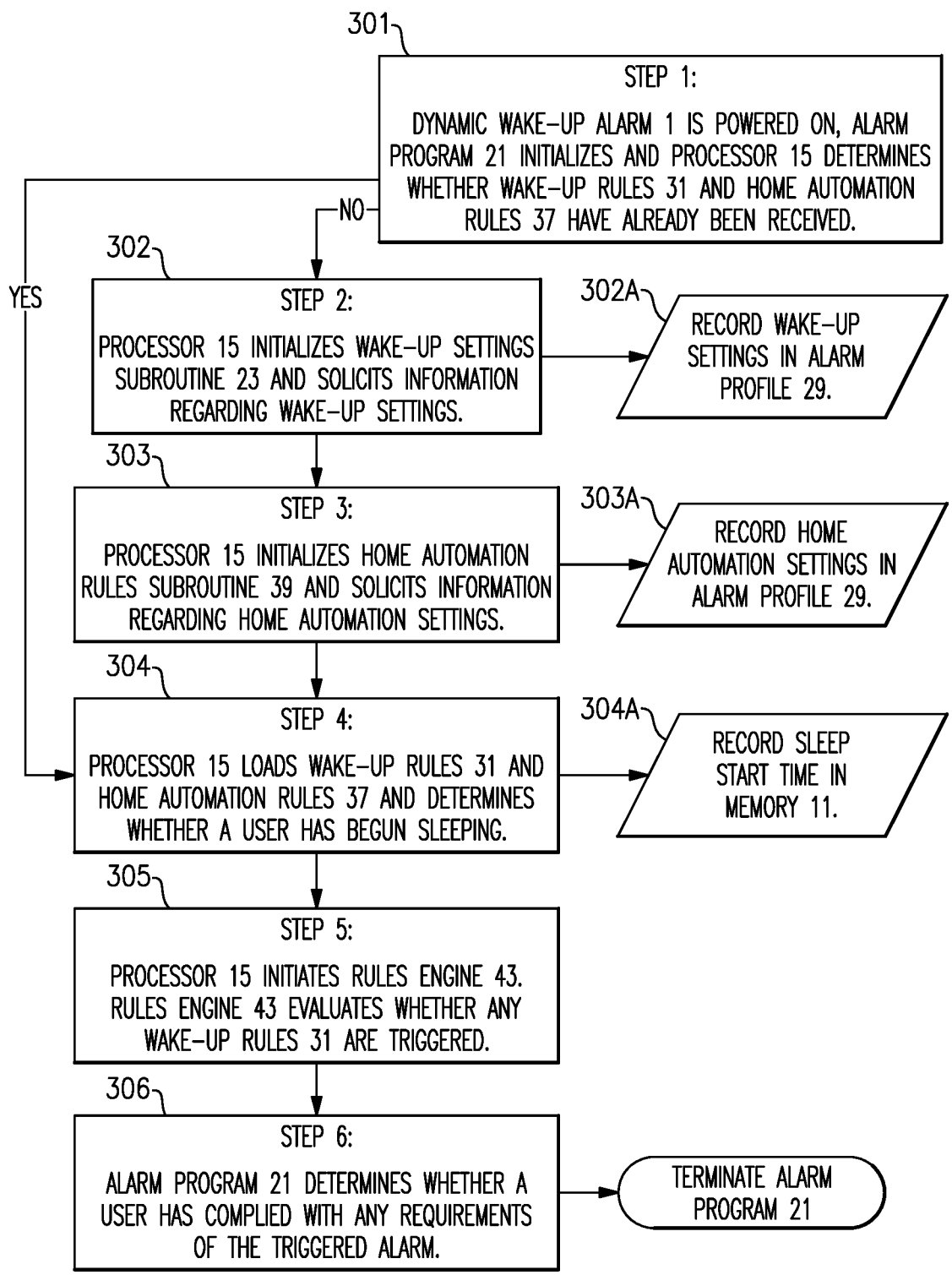
FIG. 3 is a flowchart showing a potential sequence of steps for an alarm program in one example of the present disclosure.

Referring now to FIG. 3, in some examples, processor 15 may initiate an alarm program 21 that may include a series of steps or subroutines to aid a user in setting and using a dynamic alarm. In a first step, dynamic wake-up alarm 1 may be powered on and alarm program 21 is initialized by processor 15 (box 301 in FIG. 3). During the startup procedure, processor 15 checks whether it already has wake-up rules 31 from a user stored in memory 11. If not, processor 15 may initialize a wake-up settings subroutine 23. However, if wake-up rules have previously been received by processor 15, alarm program 21 may proceed to step 3 without initializing wake-up settings subroutine 23.

In a second step, processor 15 may initialize wake-up settings subroutine 23 and load information regarding a user's wake-up settings (boxes 302 and 302A). For a first-time setup, this may include user interaction, but in general, any settings needed are loaded from memory or other sources. As explained in greater detail with respect to FIG. 4, below, during wake-up settings subroutine 23, processor 15 may solicit wake-up rules 31 from a user based on various wake-up criteria 33 for triggering an alarm, including time criteria, biometric criteria, traffic criteria, weather criteria, or any other criteria for triggering an alarm. For example, in some implementations, the wake-up criteria may include an earliest acceptable wake-up time 25 and a latest permissible wake-up time 27.

Wake-up criteria 33 may also include any information that may be observed or retrieved by dynamic wake-up alarm 1. For example, wake-up criteria 33 may include biometric factors that are observed or determined, based on information received by processor 15 from biometric sensor 19. Wake-up criteria 33 may also include information that may be retrieved from external devices or databases. For example, wake-up criteria 33 may include traffic conditions, weather conditions, home automation conditions, information retrieved from a user's calendar, or information received from other dynamic wake-up alarms within a home (e.g., information regarding the sleep state of a family member). Wake-up criteria may also include a sleep score wake-up criteria, which may allow a user to set an alarm based on the overall quality of their sleep as determined through a sleep scoring process at any given point in their sleep session.

Processor 15 may also receive wake-up rules 31 based on the various criteria available through a graphical user interface or through dropdown menus or any other method for generating logical rules known to one of ordinary skill in the art. As explained further with respect to FIG. 4, below, wake-up rules 31 may be based on any combination of wake-up criteria 33 and may define rules for sounding a wake-up alarm under various conditions. Processor 15 may also receive an alarm type associated with a given wake-up rule, which may specify the conditions under which an alarm may be shut off for a given rule. For example, based on the wake-up criteria triggering the wake-up rule, it may be necessary to sound an alarm until a user physically vacates their sleep space. In other examples, it may be necessary to deactivate the snooze feature for certain types of alarm rules 31.

At step 3, processor 15 may also load home automation rules 37 via a home automation rules subroutine 39 (box 303 and 303A). With traditional alarm clocks, it was previously possible to set in-home appliances, such as a coffee-maker, to begin running based on a set wake-up timeframe. However, with the dynamic wake-up alarm of the present disclosure, in-home appliances may be controlled based on a user's actual wake-up time, as determined by biometric sensor 19.

Home automation subroutine 39 may activate rules based on a user's actual wake-up time, or some time before it when the wake-up rules 31 can predict the wake-up time. Home automation rules 37 may also be independent of a user's actual wake-up time, based on the same criteria available for the wake-up rules 31, which, in this context, may be referred to as home automation criteria 41. As described above with respect to wake-up criteria 33, home automation criteria 41 may include any information received from biometric sensor 19, traffic or weather information, the user's calendar, or other dynamic wake-up alarms 1 throughout the home. In one example, processor 15 may receive, through home automation rules subroutine 39, a home automation rule to start a coffee maker as soon as a user awakens, or some time before the user is expected to awaken, so the coffee will be ready. Similarly, processor 15 may receive a home automation rule to pre-heat water for a shower thirty minutes after the user wakes in order to allow a user time for a morning jog. Other home automation rules may do such things as turn on lights and raise the temperatures associated with the user waking. Any combination of home automation criteria 41 may be employed to create home automation rules 37, in a manner similar to wake-up rules 31, as described above. Thus, any number of home automation tasks may be controlled based on information ascertainable by dynamic wake-up alarm 1, such as the operation of home appliances, thermostat settings, power settings, lighting, or electronic blinds, among others. Once defined, home automation rules 37 may also be stored within alarm profile 29.

At a fourth step, processor 15 loads wake-up rules 31 and home automation rules 37 that determine how to respond to wake-up criteria 33 (box 304). Processor 15 also begins monitoring whether a user has begun sleeping. To do so, processor 15 monitors a user's biometrics in order to determine when a user has fallen asleep. A full description of how sleep state may be determined (and how the same system may induce and maintain it) is found in U.S. patent application Ser. No. 15/267,464 entitled Sleep Quality Scoring and Improvement; U.S. patent application Ser. No. 15/267,567 entitled Sleep Assistance Device; U.S. patent application Ser. No. 15/267,848 entitled Sleep System; U.S. patent application Ser. No. 15/267,858 entitled User Interface for a Sleep System; and to U.S. patent application Ser. No. 15/267,886 entitled Sleep Assessment Using a Home Sleep System; all of which are filed on even date herewith and are incorporated herein by reference. Once sleep has been detected, processor 15 may log the time of sleep initiation for use in later processes, such as sleep scoring, and an in order to assess elapsed sleep time as a potential wake-up criteria 33 (box 304A).

In a fifth step, processor 15 initiates a rules engine 43 (box 305). While executing rules engine 43, processor 15 assesses the wake-up criteria 33 required to evaluate each wake-up rule 31 stored in alarm profile 29. Processor 15 periodically retrieves any necessary information from biometric sensor 19 or any applicable external sources, including home automation system, traffic, weather and calendar resources, for example. Once received, all relevant information may be stored for continual analysis by processor 15. Alarm record 35 may be implemented as a database for storing and retrieving information relevant to alarm rules 31 during a sleep session and for evaluating whether the wake-up criteria of a given wake-up rule have been met. Processor 15 then proceeds to evaluate whether the conditions of each user-defined wake-up rule or home automation rule have been met on a recurring basis. When a rule's conditions are met based on the retrieved information and the current time (if relevant), alarm program 21 initiates the alarm type specified in the applicable wake-up rule 31 or sends a signal to control the appliance specified in the applicable home automation rule 37.

At a sixth step, processor 15 determines whether a user has complied with any requirements of the triggered alarm (box 306). For example, where a specified alarm type merely requires a user to awaken, alarm processor 15 determines whether the user has done so, based on readings from biometric sensor 19. If so, processor 15 terminates the alarm. Similarly, where a specified alarm type requires a user to actually vacate the bed or sleep space, processor 15 determines whether the user has done that, again, based on readings from biometric sensor 19. Where a specified alarm type requires a mechanical shutoff, for example, by depressing a button on dynamic wake-up alarm 1, processor 15 determines whether the user has performed the required action, based on readings from buttons 8 or signals received from an external computing device. Once the requirements of the triggered alarm have been satisfied, processor 15 terminates alarm program 21 until the user has been detected returning to the sleep space for another sleep session. In some examples, more than one alarm rule may be triggered, with different criteria for shut-off. For example, a first rule may merely require that the user awaken, while a second rule requires the user to actually get out of bed. If the two rules trigger the alarm at the same time, all of their shut-off criteria may be required, or one type of criteria may take precedence. In other examples, complying with one rule's shut-off criteria may temporarily disable the alarm, only to have the second alarm sound a few minutes later if the user didn't also comply with that alarm's shut-off criteria.

Figure 4:
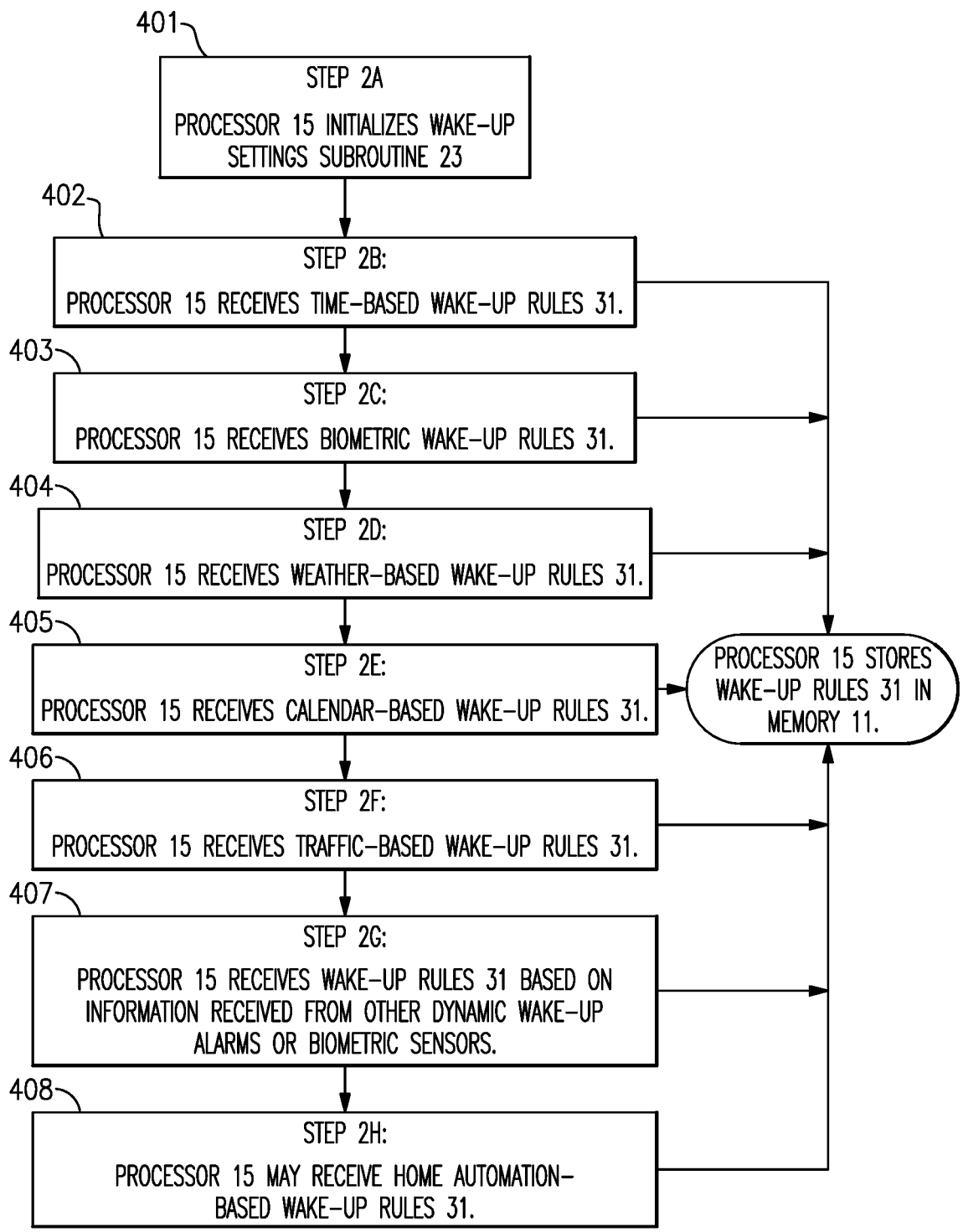
FIG. 4 is a flowchart showing a potential sequence of steps for a wake-up settings subroutine in one example of the present disclosure.

FIG. 4 is a flowchart showing a potential sequence of steps for a wake-up settings subroutine in one example of the present disclosure. At step 2A, processor 15 initializes wake-up settings subroutine 23 in order to solicit information from a user regarding alarm settings (box 401 in FIG. 4). At step 2B, processor 15 may receive wake-up rules 31 based on time-based wake-up criteria 33, such as an earliest acceptable wake-up time 25 and a latest permissible wake-up time 27, which establishes a timeframe or window in which a user desires to wake-up under normal circumstances (box 402). Different times may be determined for different days of the week or during different times of year. Once determined, the earliest acceptable wake-up time 25 and latest permissible wake-up time 27 are stored within an alarm profile 29 by processor 15. In some examples, the times are simply loaded from the existing profile 29, and the wake-up settings subroutine 23 is only activated if there is some indication that the settings have changed. Wake-up times 25 and 27 may be updated by a user at any time through an appropriate user interface.

At step 2C, processor 15 may receive wake-up rules 31 based on biometric wake-up criteria, such as a user's own biometric readings, as determined from biometric sensor 19 (box 403). For example, processor 15 may continually determine whether a user is present in bed based on readings provided by biometric sensor 19. Once a user's presence has been detected, processor 15 begins actively monitoring the user's biometrics on a continual basis in order to determine when the user has fallen asleep. To do so, processor 15 reads signals from biometric sensor 19 to determine whether there has been a measurable change in heart rate, respiration, heart rate variability, body movements, or any other biometric indicator of sleep known to one of ordinary skill in the art. Once sleep has been detected, processor 15 may log the time of sleep initiation in an alarm record 35.

Once the user has fallen asleep, processor 15 begins actively monitoring the current sleep conditions throughout the sleep session. Current sleep conditions may include any combination of biometric and environmental variables relevant to sleep which are measured throughout a sleep session. A user's biometrics are monitored by biometric sensor 19 on a continual basis in order to record any relevant variables for tracking the overall quality of a user's sleep over time. For example, variables affecting or indicative of the quality of a user's sleep include the user's heartrate, respiration rate, bodily movement, body temperature, blood pressure, sleep state (e.g. REM, N-REM, deep, or light sleep). All of the monitored biometrics may be recorded in memory 11 and used to determine an overall sleep score in a manner described in U.S. patent application Ser. No. 15/267,464 entitled Sleep Quality Scoring and Improvement (incorporated by reference, above). The sleep score may, in turn, be used as a wake-up criterion for a wake-up rule, as it shows the quality of the sleep during the sleep session.

Any of the biometric information recorded in alarm record 35, or the sleep scores derived from that information, may serve as useful wake-up criteria 33 for wake-up rules 31. For example, the system may default to a wake-up rule that states that the user should be awoken as soon as they enter a light sleep state, appropriate for waking, after the earliest acceptable wake-up time 25. The rule may further state that the alarm should only sound at the first occurrence of the light sleep state if the user has achieved a sleep score of, at least 85, for example. If the user did not sleep well, waking should be delayed. Users may modify or place additional limitations on wake-up rules 31 and there are no limits on the number of wake-up criteria 33 that may be considered together before an alarm is triggered prior to latest permissible wake-up time 27. In some implementations, biometric wake-up stimuli may include, but are not limited to, sleep quality, sleep score, sleep duration, REM duration, deep sleep duration, presence in bed, current sleep state, total heartbeats while sleeping, total breaths while sleeping, or any other observable or retrievable biometric criteria known to one of ordinary skill in the art.

At step 2D, processor 15 may receive wake-up rules 31 based on weather-based wake-up criteria 33 (box 404). For example, using a network connection, processor 15 may access weather databases and resources to retrieve current weather conditions in a user's area. Once retrieved, these weather conditions serve as useful wake-up criteria 33 in the same manner as biometric information, as discussed above. For example, a user may wish to wake-up early whenever the temperature is at least 70 degrees and the forecast calls for either "partly cloudy" or "clear" skies. Such weather-based criteria may also be combined with biometric criteria, such as a user's sleep score, as discussed above.

As one of ordinary skill in the art will appreciate, any weather-based criteria may be used as wake-up criteria 33 including, but not limited to, forecast, temperature, current precipitation totals, weather warnings, humidity, and air pressure. Weather may also serve as a useful wake-up criterion in situations where bad weather is expected that would likely cancel a user's classes or work obligations, for example. In such cases, weather-based criteria may be used to prevent an alarm from otherwise sounding in a wake-up rule. Weather criteria may also be used to delay an alarm, much like they are used to advance one, for example, letting the user sleep until closer to the latest wake-up time, if sleep score was low and the weather is bad, as opposed to waking early to take advantage of good weather.

At step 2E, processor 15 may receive wake-up rules 31 based on calendar-based wake-up criteria 33 (box 405). For example, information from a user's calendar may be received by processor 15 as wake-up criteria 33 in a wake-up rule. For example, the time of a first event on a user's work calendar may be used, in combination with travel time, to set the latest permissible wake-up time 27 to make sure the user arrives at their workplace in advance of an early meeting. The wake-up settings subroutine 23 may access information regarding a destination, a point of origin, an arrival time, and any desired buffer time in order to dynamically set their alarm for sufficient time to get ready and arrive at the destination. Such rules may help to set the latest wake-up time to ensure that a user always receives an alarm if they are in danger of missing an early morning meeting, even if they neglect to create an alarm for that particular event.

At step 2F, processor 15 may receive wake-up rules 31 based on traffic-based wake-up criteria 33 (box 406). For example, information retrieved from traffic reporting resources may be received by processor 15 as wake-up criteria 33 in order to further improve factoring of a user's commute or planned trip into a wake-up rule 31. For example, processor 15 may receive rules using traffic-based wake-up criteria that trigger a wake-up alarm as soon as a user needs to wake up in order to arrive at work on time, given the current traffic conditions along their usual commute. Such traffic-based wake-up rules could also be combined with calendar-based criteria to ensure that a user arrives at work on time for any scheduled meetings.

As one of ordinary skill in the art will appreciate, any traffic-based information may be used as wake-up stimuli 33 including, but not limited to, traffic time estimates, traffic warnings, indications of an accident along a route, and indications of planned construction along a route. Furthermore, the present disclosure is not limited to wake-up criteria 33 based on automobile traffic conditions. Any available information may be used, including public transportation timetables and flight delay information, for example.

At step 2G, processor 15 may receive wake-up rules 31 based on information received from other dynamic wake-up alarms or biometric sensors (box 407). For example, information received from a second dynamic wake-up alarm 1 within the home may cause processor 15 to sound an alarm if the second device detects biometric information of another user indicating that they may need assistance. A wake-up rule 31 may be received by processor 15 that is intended to sound when a second user is detected as having a fever, wakes up unexpectedly, or is detected as having any other health or sleep abnormalities. For example, a wake-up rule 31 could be triggered whenever a child is detected as having a temperature over 100 degrees or if they are detected as being awake during a specified timeframe. As with a primary user's biometric information, any detectable biometric information, such as those listed above, regarding a second user may be reported by a second dynamic wake-up alarm 1 to the primary user's dynamic wake-up alarm. Stand-alone biometric monitoring equipment may similarly provide information about a second user to the first user's dynamic wake-up alarm.

At step 2H, processor 15 may receive wake-up rules 31 based on information received from a home automation system (box 408). For example, information regarding the status of home equipment or in-home readings may activate a wake-up rule 31 in the event of a major equipment failure within the home. In other examples, a wake-up rule may be received by processor 15 that will be triggered if the in-home temperature drops below or rises above a pre-determined temperature, which may indicate a failure of the home heating equipment.

At each of steps 2B-2H, processor 15 may also receive a selection of an alarm type as part of a wake-up rule 31. For example, given the purpose and context of a wake-up rule 31, it may be critical that a user promptly awaken from bed and not be permitted to press the snooze button, for example if an alarm is triggered based on the status of a user's child. In such cases, the settings in alarm profile 29 may specify different alarm types for any given wake-up rule 31. As just noted, an alarm type may disable the snooze button. Other alarm types may provide a persistent alarm until a user is determined to have physically vacated their bed or sleep space, based on signals received from biometric sensor 19. In other contexts, a more traditional alarm type that incorporates a snooze function may be acceptable, based on the context of the particular wake-up rule 31 associated with the alarm.

In some implementations dynamic wake-up alarm 1 provides a gentle wake-up mode in advance of a final wake-up alarm in order to gradually raise a user's consciousness from sleep to wakefulness. A gentle wake-up mode is fully described in U.S. patent application Ser. No. 15/267,567 entitled Sleep Assistance Device (incorporated by reference, above). Thus, an alarm type may specify whether to enable the gentle wake-up feature for any given wake-up rule 31. However, based on the wake-up criteria 33 employed by a particular rule, the gentle wake-up mode may be unavailable, due to a lack of forewarning that the rule may activate an alarm. In such instances, the settings may indicate that the gentle wake-up mode is unavailable for that particular rule due to the types of wake-up criteria being employed, or this may be determined by the circumstances. In some examples, the gentle wake-up mode is preferred, and is used any time a wake-up rule is triggered for any non-emergency reason in advance of a final wake-up time.

Thus, the foregoing disclosure provides for a dynamic wake-up alarm that triggers an alarm based on wake-up rules 31 that are based, not only on the time of day, but on dynamic information observable or retrievable by the dynamic wake-up alarm. These dynamic wake-up criteria include information such as biometric information, weather information, traffic information, home automation information and biometric information relating to other users within the primary user's home. Based on the context of the wake-up rules specified, a user may also select a suitable alarm type to be triggered by the dynamic wake-up alarm 1 automatically, based on information observed by the system on an ongoing basis.

One of skill in the art will appreciate that the systems, methods and apparatuses outlined above may include various hardware and operating software, familiar to those of skill in the art, for running software programs as well as communicating with and operating any devices, including, for example, a biometric sensor, environmental sensors, a user interface, a computer network, a sound system, and any other internal or external devices. Such computerized systems may also include memory and storage media, and other internal and external components which may be used for carrying out the operations of this disclosure. Moreover, such computer systems may include one or more processors for processing and controlling the operation of the computer system, thus, embodying the processes of this disclosure. To that end, the processor, associated hardware and communications systems may carry out the various examples presented herein.

While the disclosed subject matter is described herein in terms of certain exemplary implementations, those skilled in the art will recognize that various modifications and improvements can be made to the disclosed subject matter without departing from the scope thereof. As such, the particular features claimed below and disclosed above can be combined with each other in other manners within the scope of the disclosed subject matter such that the disclosed subject matter should be recognized as also specifically directed to other implementations having any other possible permutations and combinations. It will be apparent to those skilled in the art that various modifications and variations can be made in the systems and methods of the disclosed subject matter without departing from the spirit or scope of the disclosed subject matter. Thus, it is intended that the disclosed subject matter include modifications and variations that are within the scope of the appended claims and their equivalents.

What is claimed:

1. A wake-up alarm system comprising:
a clock;
a microphone;
a processor;
memory; and
a speaker;
wherein said processor is configured to:
receive at least one wake-up rule based on at least two wake-up criteria, a first of the at least two wake-up criteria including a sleep score criterion based on data from a biometric sensor, a second of the at least two wake-up criteria being based on a time criterion comprising an earliest wake-up time,
determine whether said at least two wake-up criteria are met,
receive an alarm type associated with the at least one wake-up rule, the alarm type specifying that an alarm may be shut off by an indication that the user is waking up,
wherein said alarm type specifies that a snooze feature is disabled; and
activate the alarm if the at least two wake-up criteria are met.

2. The wake-up alarm system of claim 1, further comprising a contactless biometric sensor for determining at least one of a heart rate, a respiratory rate, a presence of a user, or movement of a user.

3. The wake-up alarm system of claim 2, wherein said processor is configured to receive at least one home automation rule based on at least one of the at least two wake-up criteria or an additional wake-up criterion; and
wherein said processor is further configured to evaluate whether the at least one of the at least two wake-up criteria or additional wake-up criterion associated with said at least one home automation rule has been met and to transmit a signal for controlling at least one home appliance based on a determination that the at least one of the at least two wake-up criteria or additional wake-up criterion associated with said at least one home automation rule has been met.

4. The wake-up alarm system of claim 1, wherein said at least one wake-up rule is further based on a third wake-up criterion comprising detection of a major equipment failure within a home of the user.

* * * * *